United States Patent [19]

Klaas

[11] Patent Number: 5,139,501
[45] Date of Patent: Aug. 18, 1992

[54] DEVICE FOR FOLDING AN ELASTIC RUBBER INTRAOCULAR LENS

[76] Inventor: Dieter Klaas, Bahnhofstrasse, 8904 Friedberg, Fed. Rep. of Germany

[21] Appl. No.: 659,966

[22] Filed: Feb. 26, 1991

[30] Foreign Application Priority Data

Dec. 7, 1990 [DE] Fed. Rep. of Germany ....... 4039119

[51] Int. Cl.⁵ ............................................... A61F 9/00
[52] U.S. Cl. ...................................... 606/107; 269/99
[58] Field of Search .................. 606/6, 1, 107, 166; 269/99, 165; 623/4, 6

[56] References Cited

U.S. PATENT DOCUMENTS

| | | | |
|---|---|---|---|
| 2,422,773 | 6/1947 | Colwill | 269/99 |
| 4,170,345 | 10/1979 | Townsend | 269/99 X |
| 4,862,885 | 9/1989 | Cumming | 606/107 |
| 4,906,247 | 3/1990 | Fritch | 606/107 X |
| 4,934,363 | 6/1990 | Smith et al. | 606/107 |
| 4,957,505 | 9/1990 | McDonald | 606/107 X |
| 4,976,716 | 12/1990 | Cumming | 606/107 |
| 5,007,913 | 4/1991 | Dulebohn et al. | 606/107 |

Primary Examiner—Peter A. Aschenbrenner
Attorney, Agent, or Firm—Fleit, Jacobson, Cohn, Price, Holman & Stern

[57] ABSTRACT

A device for folding an elastic rubber intraocular lens, has two lens gripping elements which can be moved one relative to the other and which can be brought into contact with a lens body from diametrically opposite positions on a block frame. A lens reception space is provided between the gripping elements with a base surface for the flat positioning of the lens body. The space is open from the top to permit the lens to be folded when the two lens gripping elements are brought together.

12 Claims, 1 Drawing Sheet

DEVICE FOR FOLDING AN ELASTIC RUBBER INTRAOCULAR LENS

BACKGROUND OF THE INVENTION

The invention relates to a device for folding an elastic rubber intraocular lens.

Intraocular lenses of elastic rubber material, particularly silicon lenses, and their insertion in a folded stat into the natural lens capsule remaining in the eye after a cataract operation are known in the art. The folding process is quite laborious, since due to its elastic properties the lens frequently pops out of the gripping elements of the implantation instrument while being folded. This is frequently the case when the elastic lens body is not precisely positioned between the gripping elements of the implantation instrument, which commonly takes the form of a forceps.

SUMMARY OF THE INVENTION

An object of the invention is to provide a device for folding an elastic rubber intraocular lens, which permits the lens to be easily folded and which affords a simple gripping capability and thus makes possible the precise positioning of the folded lens in an implantation instrument.

The invention provides a device for folding an elastic rubber intraocular lens, which has two lens gripping elements on top of a block frame. The elements can be displaced one relative to the other and can be brought into contact with the lens circumference from diametrically opposite positions. A lens reception space is provided between the lens gripping elements on top of the block frame, which space has a base surface for level positioning of the lens body and which space is open from the top.

When the two lens gripping elements guided on the block frame approach each other, the elastic rubber intraocular lens located between them is folded upwards, i.e. away from the base surface. The lens reception space is open from the top, thereby allowing a displacement of the lens body in the upward direction. In a preferred form of the invention one of the lens gripping elements is immovably mounted on the block frame, while the other element is guided toward it.

The lens body is engaged by the lens gripping elements along its circumferential rim and is held in place in the area of the base surface. The design of the lens gripping elements is such that when the lens body is held in a folded condition, the lens body can be grasped by an implantation instrument. For example, the folded lens can be grasped on either side with the ends of a pair of forceps, it being possible to insert the forceps between the folded lens body and the lens gripping elements. It is also possible to insert a tube-shaped implantation instrument, one that accommodates the section of the folded lens, from above the folded lens, so that the precise positioning of the folded lens body is assured during insertion of the folded lens body into the implantation instrument.

In a preferred form of the invention, the gripping elements may have attachment means on their upper side, for example in the form of projections for attachment loops forming a haptic on the lens body.

A dovetail groove can be formed in the block frame to guide both gripping elements or to guide only the movable gripping element.

The body frame can be provided as an inset in a lens storage container. In this case the lens is located in the lens reception space and is secured in level position on the base surface. The two lens gripping elements are located at diametrically opposite points on the circumference of the unstressed lens lying in flat position. In this version, the lens can be held in readiness in sterile condition, within a storage container in the block frame.

DESCRIPTION OF PREFERRED EMBODIMENT

Figure 2:
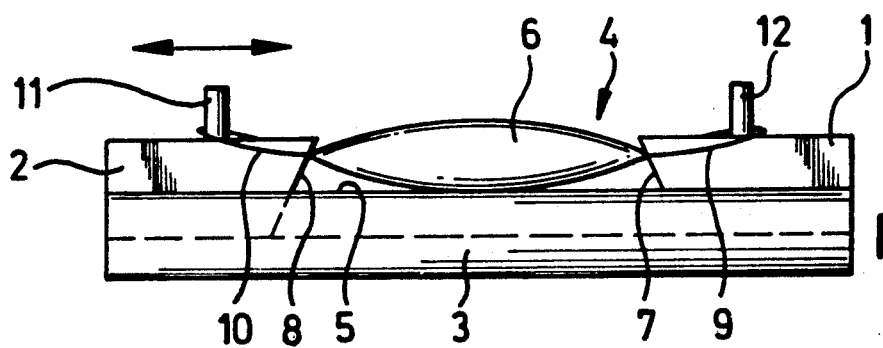
FIG. 2 is a side view of the device shown in FIG. 1, with an intraocular lens resting flat therein.

A device for folding an elastic rubber intraocular lens, as shown in the drawings, has two lens gripping elements 1 and 2. The lens gripping elements are located in diametrically opposite positions relative to a lens body 6 inserted in the device (FIG. 2). The lens gripping elements 1 and 2, which are designed as stops in the depicted embodiment, are mounted on a block frame 3. Located between the lens gripping elements 1 and 2 is a lens reception space 4 having a base surface 5, on which the lens body 6 can be placed flat for safe storage or before folding. The lens reception space 4 is open from the top. Both, or at least one, of the lens gripping elements 1 and 2 can be designed so as to be displaceable relative to the block frame 3. In the depicted embodiment, lens gripping element 2 can be displaced relative to the block frame 3 and to the other lens gripping element 1 which is immovably attached to the block frame 3. A dovetail groove 13 is provided in the block frame 3 for defined guidance of the gripping element 2 during displacement on the block frame. A sliding piece 14 is attached tot he displaceable lens gripping element 2 and is inserted into the dovetail groove 13. The block frame 3 and the lens gripping elements may consist of metal or of plastic.

Figure 3:
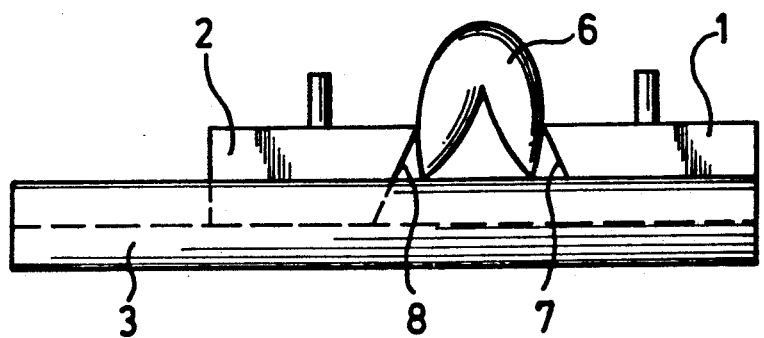
FIG. 3 is a view similar to FIG. 2 showing a position of the device with the lens folded.

As can be seen particularly in FIGS. 2 and 3, the lens gripping elements 1 and 2 have stop or gripping surfaces 7 and 8, which are undercut at an acute angle relative to the base surface 5 of the lens reception space. In this manner a secure positioning of the lens body 6 is assured during storage or folding between the two lens gripping elements 1 and 2. It is also possible for the stop surfaces 7 and 8 to be slightly concave in plan view to accommodate the circular form of the lens diameter—as can be seen in perspective view in FIG. 1.

On the upper side the lens gripping elements 1 and 2 can be provided with attachment means 11 and 12 in the form of pins for attachment loops 9 and 10, which form a haptic on the lens body 6.

In folding the lens body 6 (FIG. 3), the lens gripping element 2 is pushed to the right, with the result that the lens body 6 is arched upwards, where the lens reception space is open. In this folded condition the lens body 6 can be held secure and can be securely grasped by an implantation instrument and kept correctly in position for implantation.

Figure 1:
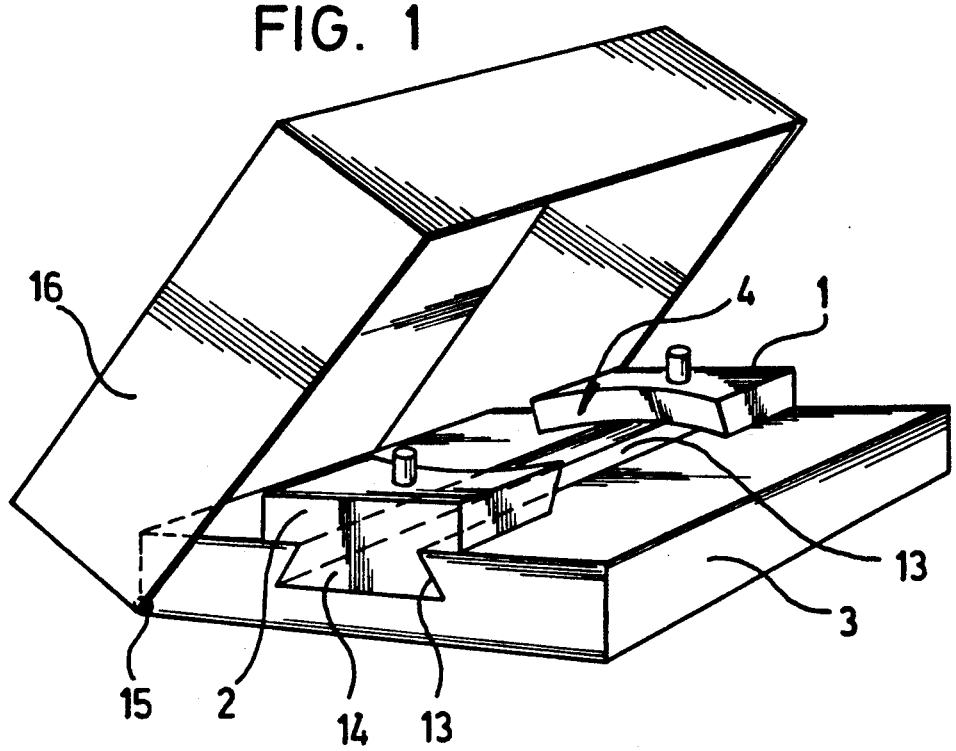
FIG. 1 is a perspective view of a lens holding and gripping device according to the invention.

As can be seen in FIG. 1, a cover or lid 16 can be articulated by means of a hinge 15 on the block frame 3, thereby permitting the folding device to be integrated into a storage container, which can be sterilized. During storage, the lens can be kept in the container and held correctly in place in flat position between the two gripping elements 1 and 2—as shown in FIG. 2.

I claim:

1. A device for folding an elastic rubber intraocular lens comprising two lens gripping elements which can be moved relative to one another and which can be brought into contact with a lens body from diametrically opposite positions, the elements being mounted on a block frame and a lens reception space being provided between the gripping elements on the frame, the reception space having a base surface for flat positioning of the lens body and being open from the top, wherein the lens gripping elements have attachment means on upper surfaces thereof for attachment loops which form a haptic on the lens body.

2. A device for folding an elastic rubber intraocular lens comprising two lens gripping elements which can be moved relative to one another and which can be brought into contact with a lens body from diametrically opposite positions, the elements being mounted on a block frame and a lens reception space being provided between the gripping elements on the frame, the reception space having a base surface for flat positioning of the lens body and being open from the top, wherein each lens element has a gripping surface concave in plan view and configured for providing an open space for access of an implantation instrument between the lens gripping element and the lens body when held in folded condition by the lens gripping elements.

3. A device as defined in claim 2, wherein a first of the lens gripping elements is immovably positioned on the block frame and a second of the lens gripping elements is mounted for guided movement on the block frame in directions toward and away from the first lens gripping element.

4. A device as defined in claim 2, wherein a dovetail groove is provided on the block frame for guidance of at least one of the lens gripping elements.

5. A device as defined in claim 2, wherein the block frame and the lens gripping elements, are integrated with a lens body flatly positioned in the lens reception space to form a reception container for storage of the lens.

6. A device for folding an elastic rubber intraocular lens comprising two lens gripping elements which can be moved relative to one another an which can be brought into contact with a lens body from diametrically opposite positions, the elements being mounted on a block frame and a lens reception space being provided between the gripping elements on the frame, the reception space having a base surface for flat positioning of the lens body and being open from the top, wherein the gripping surfaces of the lens gripping elements are concave in plan view and undercut at an acute angle relative to the base surface of the lens reception space.

7. A device as defined in claim 6, wherein a first of the lens gripping elements is immovably positioned on the block frame and a second of the lends gripping elements is mounted for guided movement on the block frame in directions toward and away from the first lens gripping element.

8. A device as defined in claim 6, wherein a dovetail groove is provided on the block frame for guidance of at least one of the lens gripping elements.

9. A device as defined in claim 6, wherein the block frame and the lends gripping elements, are integrated with a lens body flatly positioned in the lens reception space to form a reception container for storage of the lens.

10. A device as defined in claim 1, wherein a first of the lens gripping elements is immovably positioned on the block frame and a second of the lends gripping elements is mounted for guided movement on the block frame in directions toward and away from the first lens gripping element.

11. A device as defined in claim 1, wherein a dovetail groove is provided on the block frame for guidance of at least one of the lens gripping elements.

12. A device as defined in claim 1, wherein the block frame and the lends gripping elements, are integrated with a lens body flatly positioned in the lens reception space to form a reception container for storage of the lens.

* * * * *